(12) United States Patent
Dvorak et al.

(10) Patent No.: US 8,003,788 B2
(45) Date of Patent: Aug. 23, 2011

(54) PROCESS FOR SYNTHESIS OF PHENOXY DIAMINOPYRIMIDINE DERIVATIVES

(75) Inventors: Charles Alois Dvorak, Palo Alto, CA (US); Keena Lynn Green, Newark, CA (US); Gary R. Lee, Belmont, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 897 days.

(21) Appl. No.: 11/906,802

(22) Filed: Oct. 4, 2007

(65) Prior Publication Data

US 2008/0086004 A1 Apr. 10, 2008

Related U.S. Application Data

(60) Provisional application No. 60/849,203, filed on Oct. 4, 2006.

(51) Int. Cl.
*C07D 239/48* (2006.01)
*C07C 43/20* (2006.01)
(52) U.S. Cl. ......... 544/298; 544/323; 544/325; 558/388
(58) Field of Classification Search .................. 544/298, 544/324, 325, 323
See application file for complete search history.

(56) References Cited

U.S. PATENT DOCUMENTS

2005/0209260 A1 9/2005 Broka et al.

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
March, J. "Attack by Nitrogen, Formulation of Sulfonamides, S-Amino-de-chlorination," *Advanced Organic chemistry, Fourth Edition*, 1992, p. 499, paragraph 0-116.

* cited by examiner

*Primary Examiner* — Venkataraman Balasubramanian
(74) *Attorney, Agent, or Firm* — Robert C. Hall

(57) ABSTRACT

A method for preparing a compound of formula k

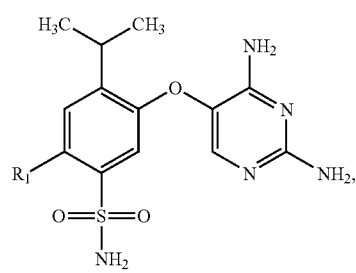

or a salt or solvate thereof,
wherein $R^1$ is as defined herein,
the method comprising treating a compound of formula j

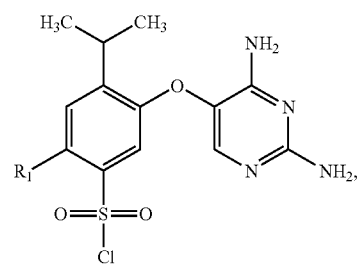

or a salt or solvate thereof,
with ammonia, to form the compound of formula k.

17 Claims, No Drawings

PROCESS FOR SYNTHESIS OF PHENOXY DIAMINOPYRIMIDINE DERIVATIVES

CROSS-REFERENCE TO RELATED APPLICATIONS

This application is entitled to the benefit of provisional patent application Ser. No. 60/849,203 filed Oct. 4, 2006, the disclosure of which is incorporated herein by reference.

FIELD OF THE INVENTION

This invention pertains to methods of making compounds for treatment of diseases associated with P2X purinergic receptors, and more particularly to methods of using $P2X_3$ and/or $P2X_{2/3}$ antagonists for treatment of genitourinary, gastrointestinal, respiratory, and pain-related diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, $P2X_1$; $P2X_2$; $P2X_3$; $P2X_4$; $P2X_5$; and $P2X_7$; and three heteromeric receptors $P2X_{2/3}$, $P2X_{4/6}$, $P2X_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic $P2X_3$ receptor subunit has also been described (Souslova, et al. (1997) Gene 195:101-111). In vitro, co-expression of $P2X_2$ and $P2X_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). $P2X_3$ receptors have been identified on nociceptive neurons in the tooth pulp (Cook et al., Nature 387:505-508 (1997)). ATP released from damaged cells may thus lead to pain by activating $P2X_3$ and/or $P2X_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that $P2X_2$ and $P2X_3$ are involved in nociception, and that modulators of P2X receptors are potentially useful as analgesics.

Other researchers have shown that $P2X_3$ receptors are expressed in human colon, and are expressed at higher levels in inflamed colon than in normal colon (Y. Yiangou et al, Neurogastroenterol Mot (2001) 13:365-69). Other researchers have implicated the $P2X_3$ receptor in detection of distension or intraluminal pressure in the intestine, and initiation of reflex contractions (X. Bian et al., J Physiol (2003) 551.1: 309-22), and have linked this to colitis (G. Wynn et al., Am J Physiol Gastrointest Liv\ er Physiol (2004) 287:G647-57); Inge Brouns et al. (Am J Respir Cell Mol Biol (2000) 23:52-61) found that $P2X_3$ receptors are expressed in pulmonary neuroepithelial bodies (NEBs), implicating the receptor in pain transmission in the lung. More recently, others have implicated $P2X_2$ and $P2X_3$ receptors in $pO_2$ detection in pulmonary NEBs (W. Rong et al., J Neurosci (2003) 23(36):11315-21).

There is accordingly a need for methods of making compounds that are effective modulators of P2X receptors, including the $P2X_3$ and $P2X_{2/3}$ receptors.

SUMMARY OF THE INVENTION

The invention provides a method for preparing a compound of formula k:

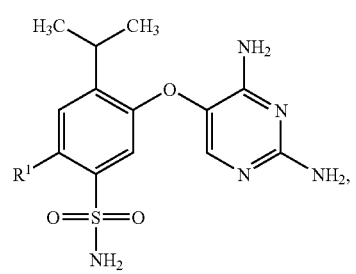

k or a salt or solvate thereof, the method comprising:
treating a compound of formula j

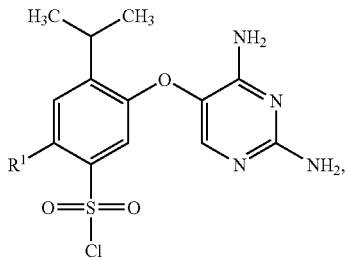

or a salt or solvate thereof,
with ammonia, to form the compound of formula k,
wherein:
$R^1$ is: hydrogen; halo; $C_{2-3}$alkynyl; halo-$C_{1-4}$alkyl; $C_{1-4}$alkoxy; hydroxy; halo-$C_{1-4}$alkoxy; hydroxy-$C_{1-4}$alkoxy; or $C_{2-3}$alkynyl-$C_{1-4}$alkyloxy.

The method is useful for preparation of compounds that are effective modulators of the $P2X_3$ and $P2X_{2/3}$ receptors. Also disclosed are compounds useful as intermediates in the methods of the invention.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R'" where where R' is alkylene, R" is —$SO_2$— and R'" is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aniline" as used herein refers to compound of the formula Ar—$NH_2$ wherein Ar is aryl or heteroaryl as defined herein. "Aniline" thus encompasses both aryl amines and heteroaryl amines generally wherein the nitrogen atom of the amino group is bound to an aromatic carbon atom. Preferred anilines are aminophenyl compounds. "Aniline" may be optionally substituted as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl" means a group of the formula —SO₂—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Brederick's reagent" as used herein means alkoxyoxybis-(dialkylamino)methane wherein the "alkyl" moieties are any lower alkyl and the alkoxy moiety is any lower alkyl. Preferably, "Brederick's reagent" is t-butoxybis(dimethylamino) methane.

"Cyanoalkyl" means a moiety of the formula —R'—R", where R' is alkylene as defined herein and R" is cyano or nitrile.

"Cycloalkyl" means a monovalent saturated carbocyclic moiety consisting of mono-or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Guanidinyl" means a compound of the formula

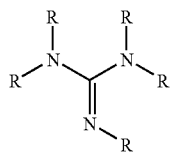

wherein each R independently is hydrogen, alkyl, a leaving group or group easily hydrolizable. R is preferably hydrogen.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" or "heteroaralkyl" means a group of the formula —R—R' wherein R is alkylene and R' is heteroaryl as defined herein.

"Heteroarylsulfonyl" means a group of the formula —SO₂—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH₂Cl, —CH₂CF₃, —CH₂CCl₃, perfluoroalkyl (e.g., —CF₃), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Polar aprotic solvent" means a solvent comprised of molecules having polar groups thereon, but without mobile protons. Exemplary polar aprotic solvents include, without limitation, dimethyl formamide, acetonitrile, dimethyl sulfoxide, N,N-dimethyl acetamide, N-methylpyrrolidinone, tetrahydrofuran, dioxane, ethyl acetate, tetrahydropyran, pyridine, acetone, 2-propanone, 2-butanone, ethylene glycol dimethyl ether, methylene chloride, chloroform, and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", "phenyl", "heteroaryl" "cycloalkyl", "heterocyclyl", or "aniline" means an aryl, phenyl, heteroaryl, cyclohexyl, heterocyclyl or aniline which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", "phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

The term "salt" or "salts" as used herein includes "pharmaceutically acceptable salts" as defined above, as well as any other salts useful in synthetic processes.

It should be understood that all references to salts or pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solution" as used herein is meant to encompass liquids wherein a reagent or reactant is present in a solvent in dissolved form (as a solute) or is present in particulate, undissolved form, or both. Thus, in a "solution", it is contemplated that the solute may not be entirely dissolved therein and solid solute may be present in dispersion or slurry form. Accordingly, a "solution" of a particular reagent or reactant is meant to encompasses slurries and dispersions, as well as solutions, of such reagents or reactants. "Solution" and "Slurry" may be used interchangeable herein.

"Solvent" as used herein is meant to encompass liquids that fully dissolve a reagent or reactant exposed to the solvent, as well as liquids which only partially dissolve the reagent or reactant or which act as dispersants for the reagent or reactant. Thus, when a particular reaction is carried out in a "solvent", it is contemplated that some or all of the reagents or reactants present may not be in dissolved form.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. A solvate may comprise differing ratios of number of molecules or moles of compound per molecule or mole of solvent present in the solvate. For example, a solvate may comprise a 1:1 relationship (mono-solvate), a 2:1 relationship (hemi-solvate), a 1:2 relationship (di-solvate, or the like, of compound to solvent.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" or "respiratory disease" refers to, without limitation, chronic obstructive pulmonary disease (COPD), asthma, bronchospasm, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center is present in a structure but no specific stereochemistry is shown, both stereoisomers associated with the chiral center are encompassed by the structure.

Methods

U.S. patent application Ser. No. 11/071,555, filed on Mar. 3, 2005, published as US2005/0209260 and incorporated herein by reference, discloses compounds effective modulators of the P2X$_3$ and P2X$_{2/3}$ receptors and uses of these compounds for treatment of P2X$_3$ and/or P2X$_{2/3}$ receptor-mediated diseases. This invention provides methods useful for preparing such compounds, and chemical intermediates useful in such methods.

The methods of the invention will be more fully understood by first referring to Scheme A below, wherein R is lower alkyl and may be the same or different in each occurrence, and Ar and R$^1$ are as defined herein. Intermediate compounds shown in brackets may, in certain embodiments, not require isolation.

SCHEME A

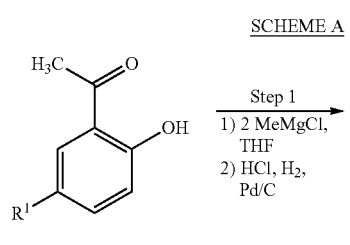

a

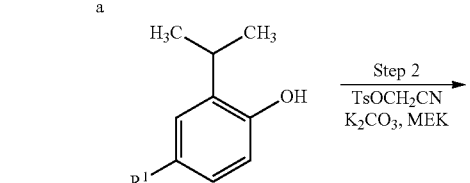

b

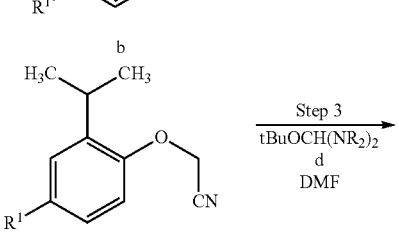

c

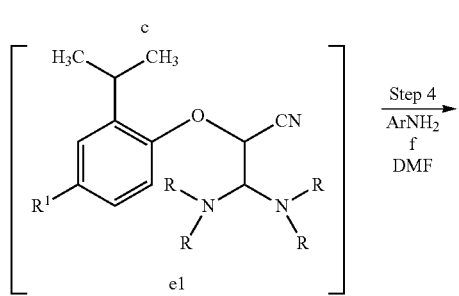

e1

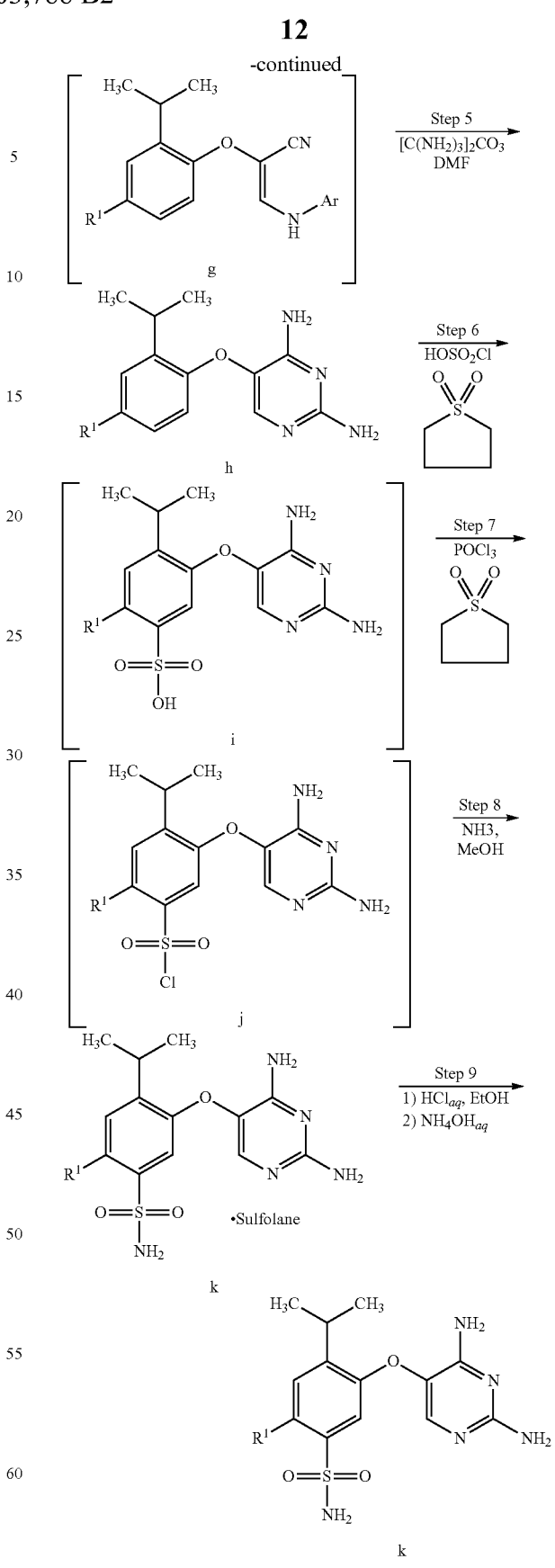

In step 1 of scheme A, acetophenone compound a is treated with a methyl Grignard reagent, such as methyl magnesium chloride or methyl magnesium bromide, followed by hydrogenation under acidic conditions, to form isopropyl phenol compound b. This reaction may be carried out, for example, under polar aprotic solvent conditions, such as in solution with THF (tetrahydrofuran), under ambient temperature conditions. Numerous acetophenone compounds a usable with the invention may be prepared by acylation of substituted phenyl compounds or by conventional techniques well known in the art. In many embodiments of the invention, the hydrogenation of step 1 may be carried out after separation and isolation of the tertiary alcohol Grignard reaction product (not shown) resulting from treatment of a with methyl grignard reagent.

In step 2, phenol compound b is treated with a cyanomethyl alkylating agent to form nitrile ether compound c. The cyanomethyl alkylating agent may be, for example, toluene-4-sulfonic acid cyanomethyl ester as shown in Scheme A. In certain embodiments bromoacetonitrile, chloroacetonitrile, or like alkylating agent may be used in place of toluene-4-sulfonic acid cyanomethyl ester. The alkylation of step 2 may be carried out under polar aprotic solvent conditions and in the presence of mild base such as potassium carbonate. In certain embodiments the reaction of cyanomethyl alkylating agent k with phenol b may be carried out as a slurry of the cyanomethyl alkylating agent, phenol b and potassium carbonate in a ketone solvent such as 2-butanone, acetone, methyl isobutyl ketone, or the like.

Cyanomethyl ether compound c is treated with Brederick's reagent d in step 3, to form an animal compound e1. This reaction may be carried out in a dimethylformamide (DMF) solution or solution of other suitable polar aprotic solvent. "Brederick's reagent" as used herein means (alkoxybis(dialkylamino)methane) generally, wherein the "alkyl" moiety R is lower alkyl and the alkoxy moiety (shown as t-butoxy in Scheme A) is lower alkoxy. In many embodiments of the invention the alkyl moiety is methyl, and the alkoxy moiety is tert-butoxy (i.e, t-butoxybis(dimethylamino)methane).

In many embodiments aminal compound e1 while in solution exists in equilibrium with cyano enamine e2 as shown below.

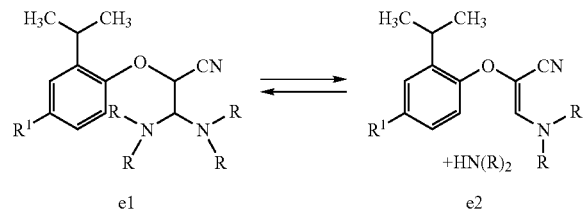

In many embodiments aminal compound e1 is not isolatable as a solid, but instead may be isolated in the form of cyano enamine compound e2. In many embodiments of the invention step 4 may be carried out directly without requiring isolation of compound e1 or e2.

In step 4, aminal compound e1 (or compound e2 or a mixture of compounds e1 and e2) is reacted with an aniline reagent f to yield aniline enamine compound g. The aniline reagent used in step 4 may comprise, for example, a compound of the formula Ar—NH$_2$ wherein Ar is optionally substituted aryl or optionally substituted heteroaryl as defined herein. The aniline reagent is preferably in salt form, such as the hydrochloride salt or other stable salt of the corresponding aniline free base. In many embodiments the aniline reagent may be a hydrochloride salt of a phenylamine of the formula:

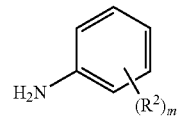

wherein m is from 0 to 4 and $R^5$ is any substituent group compatible with the solvent and reaction conditions of step 4. Preferably m is 0. The reaction of step 4 may be carried out under polar aprotic solvent conditions such as are offered by DMF. In many embodiments of the invention the aniline enamine compound g need not be isolated, and step 5 below may be carried out directly while aniline enamine h remains in solution.

In step 5, aniline enamine compound g is treated with a guanidine reagent to afford diaminopyrimidine h. The guanidine reagent may comprise, for example, guanidine carbonate or other stable salt of guanidine. The reaction of step 5 may be carried out in polar aprotic solvent such as DMF, and in many embodiments may be carried out without requiring isolation of compound g or compound e1 as noted above.

In step 6, diaminopyrimidine compound h is treated with chlorosulfonic acid to afford sulfonic acid compound i. The treatment of compound h with chlorosulfonic acid is carried out under polar aprotic solvent conditions, preferably using sulfolane (also known as tetramethylene sulfone or tetrahydrothiophene dioxide) as solvent. In many embodiments sulfonic acid compound i need not be isolated, and step 7 below may be carried out directly while sulfonic acid compound i remains in solution. Sulfonic acid compound i in many embodiments may be in salt form. Such salts of compound i include, for example, the hydrochloride salt, sulfate salt, phosphate salt, chlorosulfate salt, chlorophospate salt, or like addition salts, or solvates of such addition salts.

In step 7, sulfonic acid compound i is treated with phosphorus oxychloride to afford sulfonic acid chloride compound j. The chlorination reaction of step 7 is carried out under polar aprotic solvent conditions, preferably using sulfolane as solvent. In many embodiments, compound i may remain in solution from step 6, without being isolated prior to carrying out step 7.

In step 8, sulfonic acid chloride compound j is reacted with ammonia to yield aminosulfonyl phenoxy diaminopyrimidine compound k. This reaction may be carried out in the presence of methanol or other polar protic solvent. In many embodiments of the invention the sulfonic acid chloride compound j of step 7 may be directly treated with ammonia and methanol, without prior isolation of compound i and while compound j remains in sulfolane solution. Sulfonic acid chloride compound j in many embodiments may be in salt form. Such salts include, for example, the hydrochloride salt, sulfate salt, phosphate salt, chlorosulfate salt, chlorophospate salt, or like addition salts, or solvates thereof.

In embodiments of the invention wherein compound k remains in sulfolane during step 8, compound k may be isolated in the form of a sulfolane solvate, as shown in Scheme A. In such embodiments step 9 may be optionally carried out to de-solvate compound k. In step 9, the sulfolane solvate of compound k is treated with acid under polar protic conditions, to afford an addition salt (not shown) of compound k. The addition salt may further treated with base to provide the free amine (base) compound k. In the embodiment of Scheme A, the sulfolane solvate of compound k is treated with aqueous HCl in the presence of ethanol (forming the hydrochloride salt of compound k), followed by treatment with aqueous ammonium hydroxide, to afford compound k as a free amine base. Sulfolane solvate k may alternatively be de-solvated by treatment with water.

The procedure of Scheme A offers several important advantages. The use of phosphorus oxychloride to convert the initially formed sulfonic acid compound i to the acid chloride compound j obviates the need for use of a very large excess (ca. 10 equivalents) of chlorosulfonic acid which would otherwise be required to directly produce compound j from compound h. The chlorosulfonic acid reagent is extremely corrosive and water-reactive reagent, and the procedure of the invention facilitates isolation of the final product, significantly reduces the waste stream hazard, and reduces overall cost.

The use of sulfolane in the sulfonation of step 6, acid chloride formation of step 7 and amination of step 8 permits a homogeneous phase reaction which is easy to control and transfer at each stage of the process. Use of other polar aprotic solvent systems generally does not permit adequate control of the reaction exotherm, and results an intractable solid mass of product which cannot be readily handled at larger than bench scale operations. The sulfolane solvent system of steps 6-8 also permits rigorous exclusion of moisture from the reaction process and thus minimizes hydrolysis of the sulfonyl chloride intermediate j, which presents a serious problem in other solvent systems.

The process of the invention thus advantageously provides, inter alia:

a readily controlled solution phase addition process which minimizes exposure of the reactive sulfonyl chloride compound j;

facile temperature control of the exothermic aminolysis reaction;

production of an easily isolatable crystalline solvate of known composition;

reproducible true crystallization of a thermodynamically stable crystalline polymorph of the desolvated sulfonamide free base k from a homogeneous phase; and easy preparation of pharmaceutically relevant salts from a homogeneous phase.

Accordingly, the invention provides a method for preparing a compound of formula k

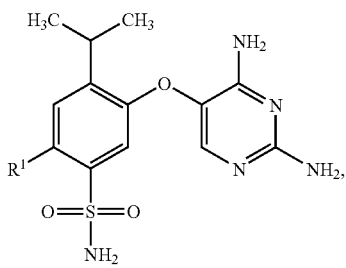

k or a salt or solvate thereof,
the method comprising:
treating a compound of formula j

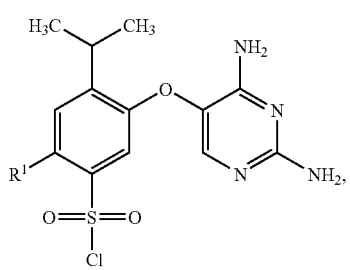

j or a salt or solvate thereof,
with ammonia, to form the compound of formula k, wherein:

$R^1$ is: hydrogen; halo; $C_{2-3}$alkynyl; halo-$C_{1-4}$alkyl; $C_{1-4}$alkoxy; hydroxy; halo-$C_{1-4}$alkoxy; hydroxy-$C_{1-4}$alkoxy; or $C_{2-3}$alkynyl-$C_{1-4}$alkyloxy.

In certain embodiments $R^1$ is: halo; $C_{1-4}$alkoxy; hydroxy; or halo-$C_{1-4}$alkoxy.

In certain embodiments $R^1$ is: halo; hydroxy; or $C_{1-4}$alkoxy.

In certain embodiments $R^1$ is chloro, bromo, hydroxy or methoxy.

In certain embodiments $R^1$ is methoxy.

In certain embodiments $R^1$ is hydroxy.

In certain embodiments the treating of the compound of formula j with ammonia is carried out in the presence of methanol.

In certain embodiments the treating of the compound of formula j with ammonia is carried out using sulfolane as a solvent.

In certain embodiments the treating of the compound of formula j with ammonia is carried out using sulfolane as a solvent, and compound k is isolated as a sulfolane solvate.

In certain embodiments the treating of the compound of formula j with ammonia is carried out using sulfolane as a solvent, and compound k is isolated as a di-solvate of sulfolane.

In certain embodiments the method of the invention further comprises:

treating a compound of formula i

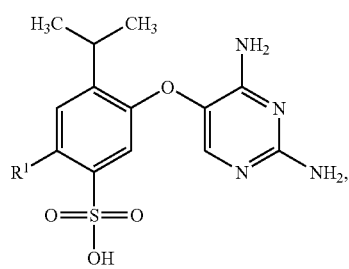

i or a salt or solvate thereof,
with phosphorus oxychloride, to form the compound of formula j. This reaction may be carried out in the presence of chlorosulfonic acid.

In certain embodiments the treating of the compound of formula I with phosphorus oxychloride is carried out using sulfolane as a solvent.

In certain embodiments the method of the invention further comprises:

treating a compound of formula h

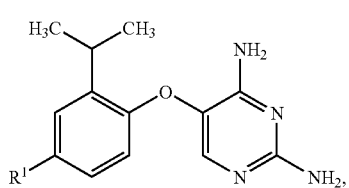

h or a salt or solvate thereof,
with chlorosulfonic acid, to form the compound of formula i.

In certain embodiments the treating of the compound of formula h with chlorosulfonic acid is carried out using sulfolane as a solvent.

In certain embodiments the method of the invention further comprises:

treating a compound of formula g g or a salt or solvate thereof, wherein Ar is optionally substituted aryl or optionally substituted heteroaryl, with a guanidine reagent, to form the compound of formula h.

In certain embodiments the guanidine reagent is guanidine carbonate.

In certain embodiments Ar is optionally substituted phenyl.

In certain embodiments the treating of the compound of formula g with guanidine reagent is carried out using dimethlyl formamide as a solvent.

In certain embodiments the method of the invention further comprises:

treating a compound of formula e1, formula e2, or a mixture thereof e1 e2 or a salt or solvate thereof,
with an aniline reagent of formula ArNH$_2$,
to form the compound of formula g.

In certain embodiments the aniline reagent is of the formula wherein m is from 0 to 4 and R$^5$ is substituent group compatible with reaction conditions for formation of the compound of formula g.

In certain embodiments m is 0.

In certain embodiments the treating a compound of formula e1, e2, or a mixture thereof with an aniline reagent is carried out using dimethyl formamide as a solvent.

In certain embodiments the method of the invention further comprises:

treating a compound of formula c c or a salt or solvate thereof,
with Brederick's reagent,
to form the compound e1, e2, or a mixture thereof.

In certain embodiments the treating a compound of formula c with an Brederick's reagent is carried out using dimethyl formamide as a solvent.

In certain embodiments the method of the invention further comprises:

treating a compound of formula b b or a salt or solvate thereof,
with a cyanomethyl alkylating agent,
to form the compound c.

In certain embodiments the cyanomethyl alkylating agent is toluene-4-sulfonic acid cyanomethyl ester.

In certain embodiments the treating of compound b with cyanomethyl alkylating agent is carried out in methyl ethyl ketone as a solvent.

In certain embodiments the method of the invention further comprises:

treating a compound of formula a a or a salt or solvate thereof,
with methyl grignard reagent, followed hydrogenation in the presence of palladium catalyst under acidic conditions,
to form the compound of formula b.

Another aspect of the invention provides a method for forming a sulfolane solvate of a compound of formula k,

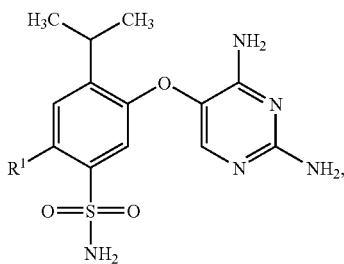

or a salt thereof,
the method comprising:
treating a compound of formula j

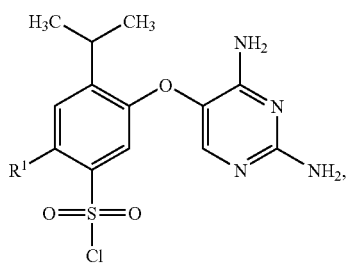

in sulfolane solvent with ammonia in the presence of methanol, to form the compound of formula k,
wherein $R^1$ is as defined herein. Preferably $R^1$ is methoxy.

In certain embodiments sulfolane solvate of the compound of formula k is a di-solvate.

In certain embodiments sulfolane solvate of the compound of formula k is a di-solvate in admixture with ammonium chloride.

Another aspect of the invention provides a method for forming a sulfolane solvate of a compound of formula k,

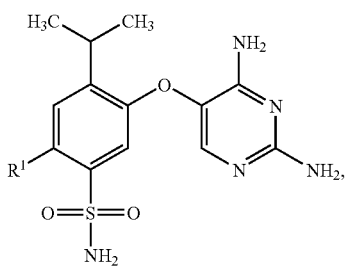

or a salt thereof,
the method comprising:
treating a compound of formula h

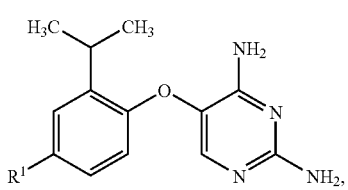

or a salt or solvate thereof,
in sulfolane solvent, with chlorosulfonic acid, followed by phosphorus oxychloride, followed by with ammonia in the presence of methanol, to form the compound of formula k.

The invention also provides a method for preparing a compound of formula k

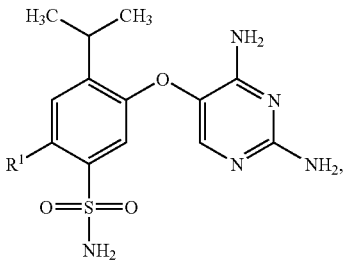

or a salt or solvate thereof,
wherein $R^1$ is hydrogen; halo; $C_{2-3}$alkynyl; halo-$C_{1-4}$alkyl; $C_{1-4}$alkoxy; hydroxy; halo-$C_{1-4}$alkoxy; hydroxy-$C_{1-4}$alkoxy; or $C_{2-3}$alkynyl-$C_{1-4}$alkyloxy;
comprising
(a) treating a compound of formula a

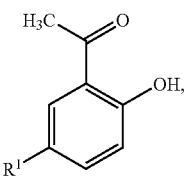

or a salt or solvate thereof,
with methyl grignard reagent, followed by hydrogenation in the presence of a palladium catalyst under acidic conditions, to form a compound of formula b

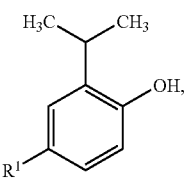

or a salt or solvate thereof,
(b) treating the compound of formula b with a cyanomethyl alkylating agent, to form a compound c,

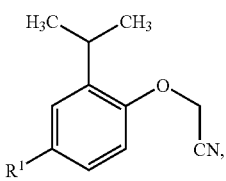

or a salt or solvate thereof, (c) treating the compound of formula c with Brederick's reagent, to form a compound e1, e2, or a mixture thereof,

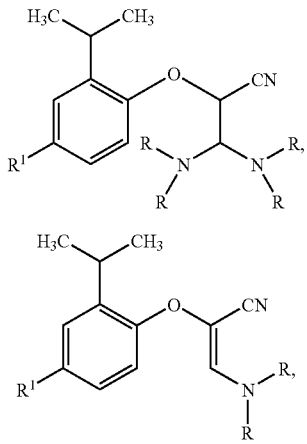

or a salt or solvate thereof, (d) treating the compound of formula e1, e2, or the mixture thereof with an aniline reagent of formula ArNH$_2$, to form a compound of formula g

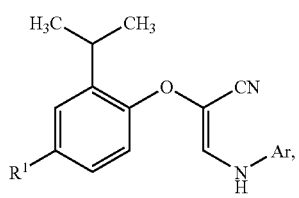

or a salt or solvate thereof, wherein Ar is optionally substituted aryl or optionally substituted heteroaryl, (e) treating the compound of formula g with a guanidine reagent, to form a compound of formula h

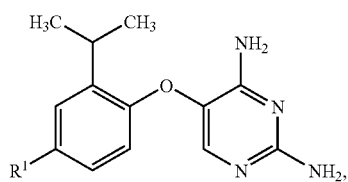

or a salt or solvate thereof, (f) treating the compound of formula h with chlorosulfonic acid, to form a compound of formula i

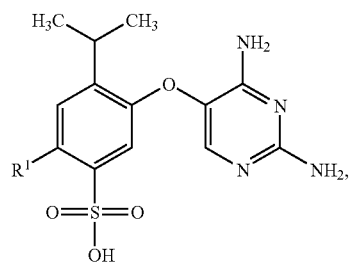

or a salt or solvate thereof, (g) treating the compound of formula i with phosphorus oxychloride, to form a compound of formula j

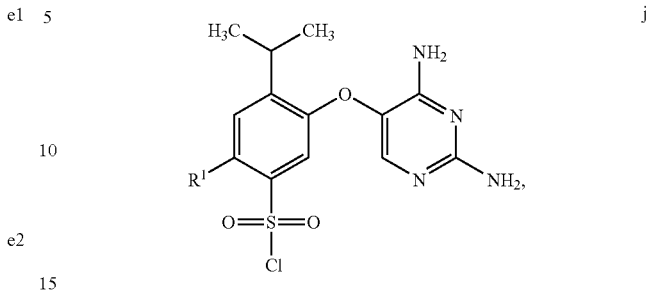

or a salt or solvate thereof, and (h) treating the compound of formula j with ammonia.

Where either of $R^1$ or $R^2$ is alkyl or contains an alkyl moiety, such alkyl is preferably lower alkyl, i.e. $C_1$-$C_6$alkyl, and more preferably $C_1$-$C_4$alkyl.

Compounds

The invention provides compounds of the formula i

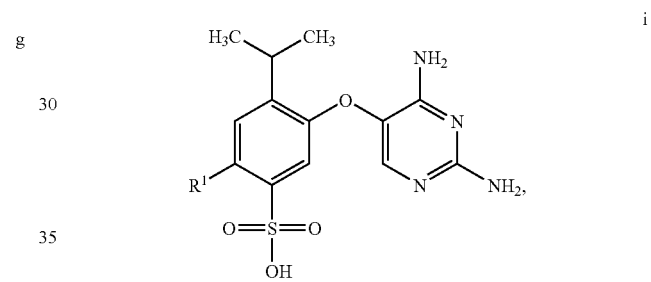

or a salt thereof, in admixture with sulfolane, wherein $R^1$ is as defined herein.

In certain embodiments the compound of formula i is an addition salt. Preferably the compound of formula i is a sulfate ($H_2SO_4$) salt.

The invention also provides compounds of the formula j

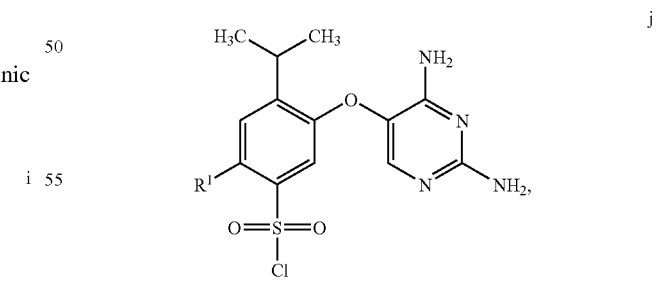

or a salt thereof, in admixture with sulfolane, wherein $R^1$ is as defined herein.

In certain embodiments the compound of formula j is an addition salt. Preferably the compound of formula i is a sulfate ($H_2SO_4$) salt.

The invention also provides compounds of the formula k

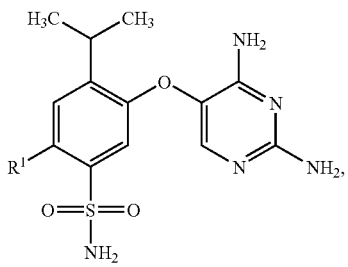

or a salt thereof,
in admixture with sulfolane or as a sulfolane solvate,
wherein $R^1$ is as defined herein.

In certain embodiments the compound of formula k is a disolvate of sulfolane.

In certain embodiments the sulfolane solvate of compound of formula j is in admixture with ammonium chloride.

In certain embodiments the compound of formula j is a di-solvate of sulfolane in admixture with ammonium chloride.

Specific details for the methods of the invention are described in the Examples section below.

Utility

The methods and compounds of the invention are useful for preparation of compounds that in turn are usable for the treatment of a wide range of genitourinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The methods and compounds of the invention are useful for preparation of compounds that in turn are usable for the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The methods and compounds of the invention are useful for preparation of compounds that in turn are usable for treating respiratory disorders, including chronic obstructive pulmonary disorder (COPD), asthma, bronchospasm, and the like.

Additionally, methods and compounds of the invention are useful for preparing compounds for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

The compounds of the invention in particular find industrial application as intermediates in the synthesis of compounds useful for the above treatments.

EXAMPLES

The following examples are given to enable those skilled in the art to more clearly understand and to practice the present invention. They should not be considered as limiting the scope of the invention, but merely as being illustrative and representative thereof. The following abbreviations may be used in the Examples.

Abbreviations

HPLC high pressure liquid chromatography
DCM dichloromethane/methylene chloride
DMF N,N-dimethylformamide
DMAP 4-dimethylaminopyridine
EtOAc ethyl acetate
EtOH ethanol
$Et_2O$ diethyl ether
gc gas chromatography
HMPA hexamethylphosphoramide
hplc high performance liquid chromatography
mCPBA m-chloroperbenzoic acid
MeCN acetonitrile
MeOH methanol
NMP N-methyl pyrrolidinone
TEA triethylamine
THF tetrahydrofuran
LDA lithium diisopropylamine
TLC thin layer chromatography

Example 1

5-(2,4-Diamino-pyrimidin-5-yloxy)-4-isopropyl-2-methoxy-benzenesulfonamide

The synthetic procedure used in this Example is outlined in Scheme B.

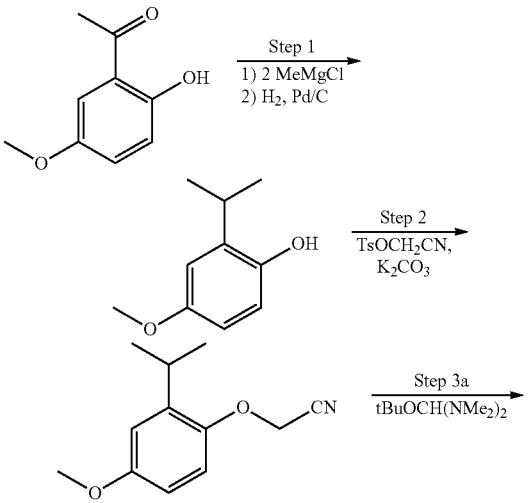

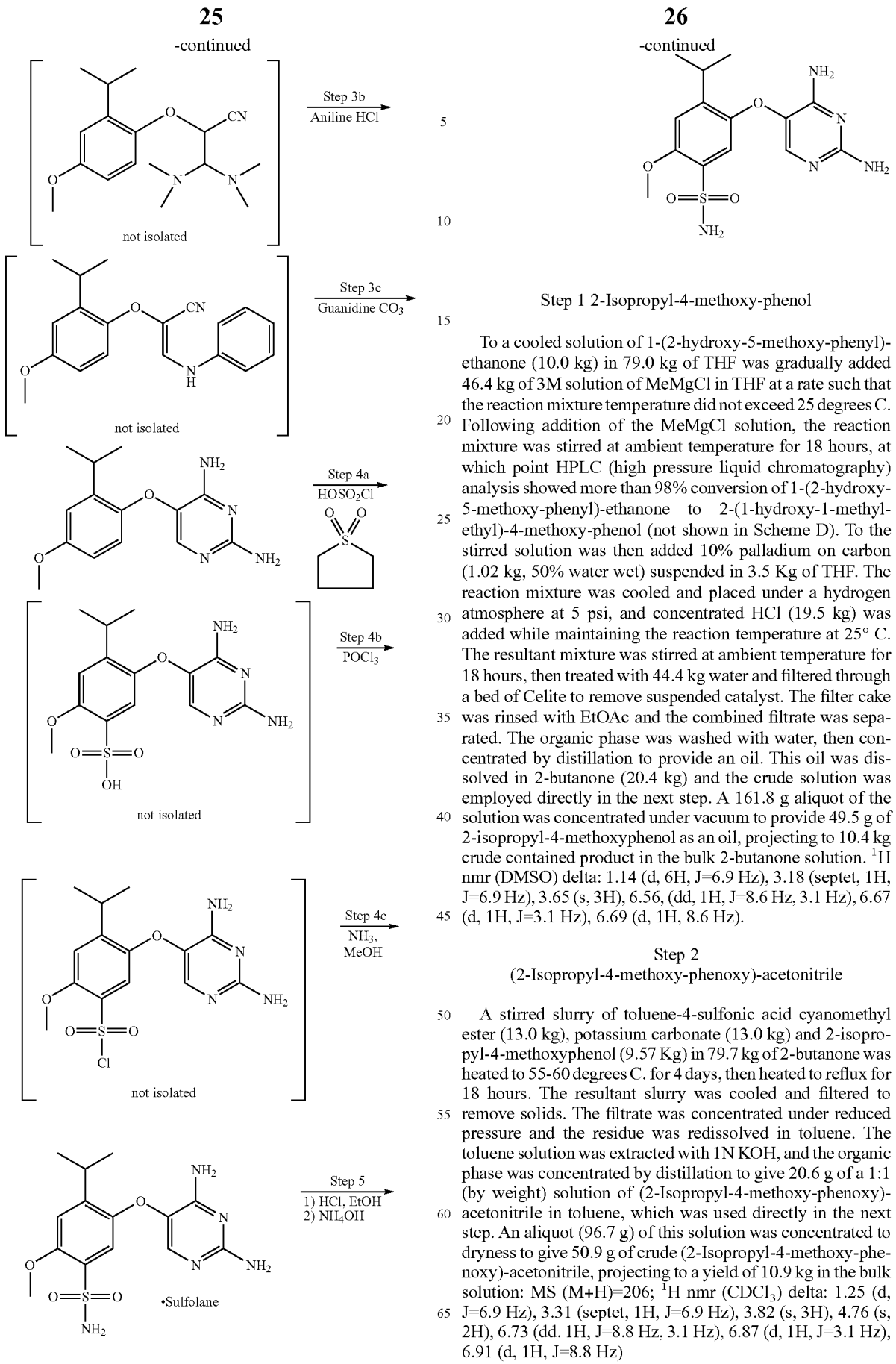

Step 1 2-Isopropyl-4-methoxy-phenol

To a cooled solution of 1-(2-hydroxy-5-methoxy-phenyl)-ethanone (10.0 kg) in 79.0 kg of THF was gradually added 46.4 kg of 3M solution of MeMgCl in THF at a rate such that the reaction mixture temperature did not exceed 25 degrees C. Following addition of the MeMgCl solution, the reaction mixture was stirred at ambient temperature for 18 hours, at which point HPLC (high pressure liquid chromatography) analysis showed more than 98% conversion of 1-(2-hydroxy-5-methoxy-phenyl)-ethanone to 2-(1-hydroxy-1-methyl-ethyl)-4-methoxy-phenol (not shown in Scheme D). To the stirred solution was then added 10% palladium on carbon (1.02 kg, 50% water wet) suspended in 3.5 Kg of THF. The reaction mixture was cooled and placed under a hydrogen atmosphere at 5 psi, and concentrated HCl (19.5 kg) was added while maintaining the reaction temperature at 25° C. The resultant mixture was stirred at ambient temperature for 18 hours, then treated with 44.4 kg water and filtered through a bed of Celite to remove suspended catalyst. The filter cake was rinsed with EtOAc and the combined filtrate was separated. The organic phase was washed with water, then concentrated by distillation to provide an oil. This oil was dissolved in 2-butanone (20.4 kg) and the crude solution was employed directly in the next step. A 161.8 g aliquot of the solution was concentrated under vacuum to provide 49.5 g of 2-isopropyl-4-methoxyphenol as an oil, projecting to 10.4 kg crude contained product in the bulk 2-butanone solution. $^1$H nmr (DMSO) delta: 1.14 (d, 6H, J=6.9 Hz), 3.18 (septet, 1H, J=6.9 Hz), 3.65 (s, 3H), 6.56, (dd, 1H, J=8.6 Hz, 3.1 Hz), 6.67 (d, 1H, J=3.1 Hz), 6.69 (d, 1H, 8.6 Hz).

Step 2
(2-Isopropyl-4-methoxy-phenoxy)-acetonitrile

A stirred slurry of toluene-4-sulfonic acid cyanomethyl ester (13.0 kg), potassium carbonate (13.0 kg) and 2-isopropyl-4-methoxyphenol (9.57 Kg) in 79.7 kg of 2-butanone was heated to 55-60 degrees C. for 4 days, then heated to reflux for 18 hours. The resultant slurry was cooled and filtered to remove solids. The filtrate was concentrated under reduced pressure and the residue was redissolved in toluene. The toluene solution was extracted with 1N KOH, and the organic phase was concentrated by distillation to give 20.6 g of a 1:1 (by weight) solution of (2-Isopropyl-4-methoxy-phenoxy)-acetonitrile in toluene, which was used directly in the next step. An aliquot (96.7 g) of this solution was concentrated to dryness to give 50.9 g of crude (2-Isopropyl-4-methoxy-phenoxy)-acetonitrile, projecting to a yield of 10.9 kg in the bulk solution: MS (M+H)=206; $^1$H nmr (CDCl$_3$) delta: 1.25 (d, J=6.9 Hz), 3.31 (septet, 1H, J=6.9 Hz), 3.82 (s, 3H), 4.76 (s, 2H), 6.73 (dd. 1H, J=8.8 Hz, 3.1 Hz), 6.87 (d, 1H, J=3.1 Hz), 6.91 (d, 1H, J=8.8 Hz)

Step 3 5-(2-Isopropyl-4-methoxy-phenoxy)-pyrimidine-2,4-diamine

An approximately 1:1 (by weight) solution of 10.6 kg of (2-Isopropyl-4-methoxy-phenoxy)-acetonitrile in toluene was concentrated under reduced pressure and the residue was treated with 10.8 kg of tert-butoxybis(dimethylamino)methane (Brederick's Reagent). The resulting mixture was dissolved in 20.2 kg of DMF and the solution was heated to 110 degrees C. for 2 hours, at which point HPLC analysis showed essentially complete conversion to 3,3-Bis-dimethylamino-2-(2-isopropyl-4-methoxy-phenoxy)-propionitrile (not isolated, $^1$H nmr (CDCl$_3$) delta: 1.21 (d, 3H, J=7.2 Hz), 1.23 (d, 3H, J=7.1 Hz), 2.46 (s, 6H), 2.48 (s, 6H), 3.43 (d, 1H, J=5.0 Hz), 3.31 (septet, 1H, J=6.9 Hz), 3.79 (s, 3H), 4.93 (d, 1H, J=5.0 Hz), 6.70 (dd, 1H, J=8.8 Hz, 3.0 Hz), 6.82 (d, 1H, J=3.0 Hz), 6.98 (d, 1H, J=8.8 Hz).

The DMF solution was cooled and transferred onto 14.7 kg of aniline hydrochloride. The resulting mixture was heated to 120 degrees C. for 22 hours, at which point HPLC analysis showed greater than 97% conversion to 2-(2-Isopropyl-4-methoxy-phenoxy)-3-phenylamino-acrylonitrile (not isolated, $^1$H nmr (CDCl$_3$) delta: 1.31 (d, 6H, J=6.9 Hz), 3.39 (septet, 1H, J=6.9 Hz), 3.82 (s, 3H), 6.61 (d (br), 1H, J=12.7 Hz), 6.73 (dd, 1H, J=8.9 Hz, 3.1 Hz), 6.88 (d, 1H, J=3.0 Hz), 6.93 (m, 2H), 6.97 (d, 1H, J=8.9 Hz), 7.05 (m, 1H), 7.17 (d, 1H, J=12.6 Hz), 7.35 (m. 2H)).

The mixture was cooled, diluted with 21.5 kg toluene, then with 72.2 L of water. The organic layer was separated, washed with water, and concentrated by distillation. The concentrate was transferred into 23.8 kg DMF, and the DMF solution was transferred onto 6.01 kg of guanidine carbonate. The resulting mixture was heated to 120 degrees C. for 3 days, at which point HPLC analysis showed greater than 95% conversion of 2-(2-Isopropyl-4-methoxy-phenoxy)-3-phenylamino-acrylonitrile into 5-(2-Isopropyl-4-methoxy-phenoxy)-pyrimidine-2,4-diamine.

The reaction mixture was cooled, diluted with 7.8 kg of EtOAc, then reheated to 60 degrees C. Water (75.1 L) was added and the resultant mixture was allowed to cool to ambient temperature. The precipitated solid was collected by filtration, rinsed with isopropanol and dried under vacuum at 50 degrees to give 9.62 kg of 5-(2-isopropyl-4-methoxy-phenoxy)-pyrimidine-2,4-diamine: m.p. 170-171 degrees C.; MS (M+H)=275; $^1$H nmr (chloroform) delta: 1.25 (d, 6H, J=6.9 Hz), 3.30 (septet, 1H, J=6.9 Hz), 3.79 (s, 3H), 4.68 (br, 2H), 4.96 (br, 2H), 6.64 (dd, 1H, J=8.9 Hz, 3.0 Hz), 6.73, d, J=8.9 Hz), 6.85 (d, 1H, J=3 Hz), 7.47 (s, 1H).

Step 4 5-(2,4-diamino-pyrimidin-5-yloxy)-4-isopropyl-2-methoxy-benzenesulfonamide, sulfolane solvate Chlorosulfonic acid (13.82 kg) was added to a slurry of 5-(2-isopropyl-4-methoxy-phenoxy)-pyrimidine-2,4-diamine (10.07 kg) in sulfolane (50.0 kg) at a rate to maintain an internal pot temperature below 65° C. The reaction mixture was aged at 60-65° C. for 12 hours, at which point HPLCL showed that all 5-(2-isopropyl-4-methoxy-phenoxy)-pyrimidine-2,4-diamine starting material had been converted to 5-(2,4-diamino-pyrimidin-5-yloxy)-4-isopropyl-2-methoxy-benzenesulfonic acid. MS (M+H)=355.

Phosphorus oxychloride (3.41 kg) was then added to the reaction mixture at 60° C. The reaction mixture was heated to 75° C. and aged for 12 hours, at which point HPLC showed that approximately 99% of 5-(2,4-diamino-pyrimidin-5-yloxy)-4-isopropyl-2-methoxy-benzenesulfonic acid had been converted to 5-(2,4-diamino-pyrimidin-5-yloxy)-4-isopropyl-2-methoxy-benzenesulfonyl chloride. MS (M+H)=373. The solution of 5-(2,4-diamino-pyrimidin-5-yloxy)-4-isopropyl-2-methoxy-benzenesulfonyl chloride was then cooled to around 2 degrees C.).

To a cooled (ca. 2 degrees C.) solution of ammonia (7N) in MeOH (74.1 kg) was added the cooled sulfolane solution of 5-(2,4-diamino-pyrimidin-5-yloxy)-4-isopropyl-2-methoxy-benzenesulfonyl chloride (a homogeneous syrup) at a rate such that the internal temperature did not exceed 23 degrees C. The resultant slurry was stirred for 18 hours at ambient temperature, then filtered on a coarse porosity frit filter. The collected solids were rinsed with MeOH (15.9 kg), then dried under reduced pressure at 70 degrees C. to a constant weight of 23.90 kg. HPLC showed 97.5% conversion of 5-(2,4-diamino-pyrimidin-5-yloxy)-4-isopropyl-2-methoxy-benzenesulfonyl chloride to 5-(2,4-diamino-pyrimidin-5-yloxy)-4-isopropyl-2-methoxy-benzenesulfonamide sulfolane solvate. $^1$H nmr (DMSO-d$_6$) delta: 1.26 (d, 6H, J=6.9 Hz), 2.07 (sym. m, 8H), 2.99 (sym. m, 8H), 3.41 (septet, 1H, J=6.9 Hz), 3.89 (s, 3H), 6.03 (s (br), 2H), 6.58 (s (br), 2H), 7.00 (s, 1H), 7.04 (s (br), 2H), 7.08 (s, 1H), 7.35 (s, 1H).

Step 5 5-(2,4-diamino-pyrimidin-5-yloxy)-4-isopropyl-2-methoxy-benzenesulfonamide A slurry of 5-(2,4-diamino-pyrimidin-5-yloxy)-4-isopropyl-2-methoxy-benzenesulfonamide sulfolane solvate (23.86 kg) in a mixture of ethanol (74.3 kg) and 0.44 N HCl (109.4 kg) was heated to reflux to provide a homogeneous solution of the monohydrochloride salt of 5-(2,4-diamino-pyrimidin-5-yloxy)-4-isopropyl-2-methoxy-benzenesulfonamide. This solution was filtered while hot, then treated with concentrated ammonium hydroxide (3.4 L) to liberate the free base of 5-(2,4-diamino-pyrimidin-5-yloxy)-4-isopropyl-2-methoxy-benzenesulfonamide. The resultant mixture was cooled slowly to 20 degrees C. and the crystalline product isolated by filtration. The filter cake was washed with water (20.1 kg) and dried under reduced pressure at 70 degrees C. to a constant weight of 8.17 kg (57.7% yield based on di-solvate of sulfolane). MP=281-282° C. $^1$H nmr (DMSO-d$_6$) delta: 1.27 (d, 6H, J=6.9 Hz), 3.41 (septet, 1H, J=6.9 Hz), 3.89 (s, 3H), 5.87 (s (br), 2H), 6.40 (s (br), 2H), 6.98 (s, 1H), 7.01 (s (br), 2H), 7.07 (s, 1H), 7.36 (s, 1H).

Example 2

P2X$_3$/P2X$_{2/3}$ FLIPR (Fluorometric Imaging Plate Reader) Assay

CHO-K1 cells were transfected with cloned rat P2X$_3$ or human P2X$_{2/3}$ receptor subunits and passaged in flasks. 18-24 hours before the FLIPR experiment, cells were released from their flasks, centrifuged, and resuspended in nutrient medium at 2.5×10$^5$ cells/ml. The cells were aliquoted into black-walled 96-well plates at a density of 50,000 cells/well and incubated overnight in 5% CO$_2$ at 37° C. On the day of the experiment, cells were washed in FLIPR buffer (calcium- and magnesium-free Hank's balanced salt solution, 10 mM HEPES, 2 mM CaCl$_2$, 2.5 mM probenecid; FB). Each well received 100 μl FB and 100 μl of the fluorescent dye Fluo-3 AM [2 μM final conc.]. After a 1 hour dye loading incubation at 37° C., the cells were washed 4 times with FB, and a final 75 μl/well FB was left in each well.

Test compounds (dissolved in DMSO at 10 mM and serially diluted with FB) or vehicle were added to each well (25 μl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 μl/well agonist or vehicle addition. The agonist was a 2× solution of α,β-meATP producing a final concentration of 1 μM (P2X$_3$) or 5 μM (P2X$_{2/3}$). Fluorescence was measured for an additional 2 minutes at 1 second intervals after agonist addition. A final addition of ionomycin (5 μM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the P2X$_3$ receptor. Using the above assay, the compound 5-(2,4-diamino-pyrimidin-5-yloxy)-4-isopropyl-2-methoxy-benzenesulfonamide exhibited a pIC$_{50}$ of approximately 7.93 for the P2X$_3$ receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for preparing a compound of formula k

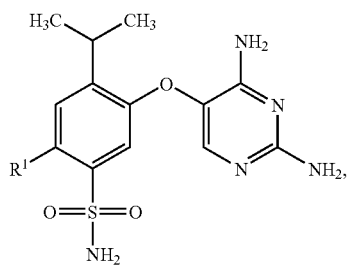

k or a salt or sulfolane solvate thereof,
the method comprising:
treating a compound of formula j

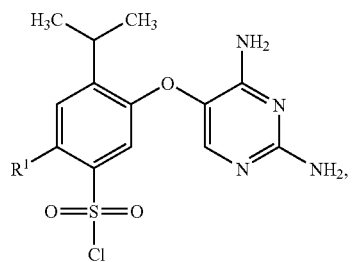

j or a salt thereof,
with ammonia, to form the compound of formula k,
wherein:
R$^1$ is: hydrogen; or C$_{1-4}$alkoxy.

2. The method of claim 1, wherein R$^1$ is methoxy.

3. The method of claim 1, wherein the treating of the compound of formula j with ammonia is carried out in the presence of methanol.

4. The method of claim 1, wherein the treating of the compound of formula j with ammonia is carried out using sulfolane as a solvent.

5. The method of claim 1, wherein the treating of the compound of formula j with ammonia is carried out using sulfolane as a solvent, and wherein compound k is isolated as a sulfolane solvate.

6. The method of claim 1, wherein the method further comprises:
treating a compound of formula i

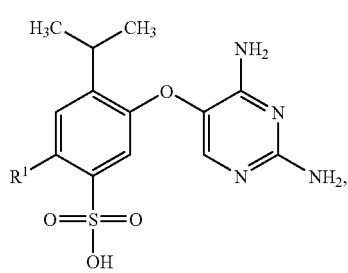

i or a salt thereof,
with phosphorus oxychloride, to form the compound of formula j.

7. The method of claim 6, wherein the treating of the compound of formula i with phosphorus oxychloride is carried out using sulfolane as a solvent.

8. The method of claim 6, wherein the method further comprises:
treating a compound of formula h

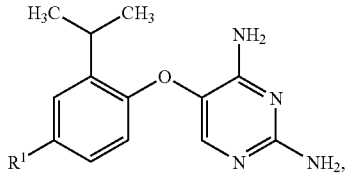

h or a salt thereof,
with chlorosulfonic acid, to form the compound of formula i.

9. The method of claim 8, wherein the treating of the compound of formula h with chlorosulfonic acid is carried out using sulfolane as a solvent.

10. The method of claim 1, wherein the method further comprises:
treating a compound of formula g

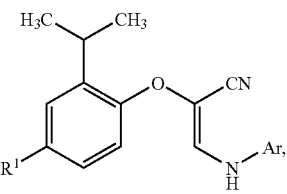

g or a salt thereof,
wherein Ar is optionally substituted aryl or optionally substituted heteroaryl,
with a guanidine reagent, to form the compound of formula h.

11. The method of claim 10, wherein the method further comprises:

treating a compound of formula e1, e2, or a mixture thereof

*[structure e1: 2-isopropylphenyl ether with CN and N(R)₂ groups, R¹ substituent]* e1

*[structure e2: vinyl ether analog with CN and NR₂ groups]* e2 or a salt thereof, wherein R is $C_{1-6}$alkyl, with an aniline reagent of formula $ArNH_2$, to form the compound of formula g.

12. The method of claim 11, wherein the method further comprises:

treating a compound of formula c

*[structure c: 2-isopropylphenyl O-CH₂-CN with R¹ substituent]* c or a salt thereof, with Brederick's reagent, to form the compound e1, e2, or the mixture thereof.

13. The method of claim 12, wherein the method of the invention further comprises:

treating a compound of formula b

*[structure b: 2-isopropylphenol with R¹ substituent]* b or a salt thereof, with a cyanomethyl alkylating agent, to form the compound c.

14. The method of claim 13, wherein the method of the invention further comprises:

treating a compound of formula a

*[structure a: 2-hydroxy-acetophenone with R¹ substituent]* a or a salt thereof, with methyl grignard reagent, followed hydrogenation in the presence of palladium catalyst under acidic conditions, to form the compound of formula b.

15. A method for forming a sulfolane solvate of a compound of formula k,

*[structure k: 4-isopropyl-pyrimidinyloxy-benzenesulfonamide with R¹ substituent and diaminopyrimidine]* k or a salt thereof, wherein:

$R^1$ is: hydrogen; or $C_{1-4}$alkoxy;

the method comprising:

treating a compound of formula j

*[structure j: analogous sulfonyl chloride compound]* j or a salt thereof, in sulfolane solvent, with ammonia in the presence of methanol, to form the compound of formula k.

16. A method for forming a sulfolane solvate of a compound of formula k,

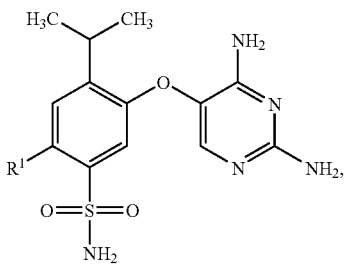

or a salt thereof,
wherein:
  $R^1$ is: hydrogen; or $C_{1-4}$alkoxy;
the method comprising:
  treating a compound of formula h

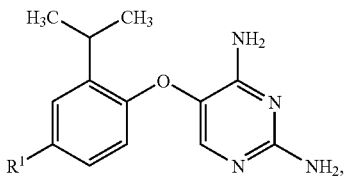

or a salt thereof, in sulfolane solvent, with chlorosulfonic acid, followed by treating with phosphorus oxychloride, followed by treating with ammonia in the presence of methanol, to form the compound of formula k.

17. A sulfolane solvate of a compound of formula k

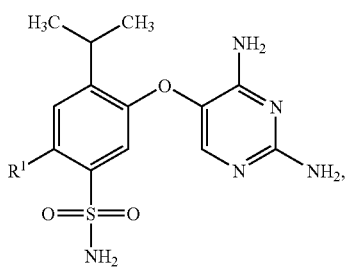

or a salt thereof,
wherein:
  $R^1$ is: hydrogen; or $C_{1-4}$alkoxy.

* * * * *